United States Patent
Aslinia et al.

(10) Patent No.: US 10,813,656 B2
(45) Date of Patent: Oct. 27, 2020

(54) EXPANDABLE ENDOSCOPIC DEVICE

(71) Applicant: UNIVERSITY OF MARYLAND, BALTIMORE, Baltimore, MD (US)

(72) Inventors: Florence M. Aslinia, Bloomington, IN (US); Eric Goldberg, Dayton, MD (US); Chad Schneider, Owings Mills, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 161 days.

(21) Appl. No.: 16/188,961

(22) Filed: Nov. 13, 2018

(65) Prior Publication Data

US 2019/0083117 A1    Mar. 21, 2019

Related U.S. Application Data

(63) Continuation of application No. 15/114,030, filed as application No. PCT/US2015/013216 on Jan. 28, 2015, now Pat. No. 10,154,851.

(Continued)

(51) Int. Cl.
*A61B 17/29* (2006.01)
*A61B 10/06* (2006.01)
(Continued)

(52) U.S. Cl.
CPC ............. *A61B 17/29* (2013.01); *A61B 10/04* (2013.01); *A61B 10/06* (2013.01); *A61B 17/10* (2013.01);
(Continued)

(58) Field of Classification Search
CPC . A61B 17/10; A61B 17/22031; A61B 17/221; A61B 17/29; A61B 10/04; A61B 10/06
See application file for complete search history.

(56) References Cited

U.S. PATENT DOCUMENTS

| 5,009,657 | A |   | 4/1991 | Cotey et al. |
| 5,514,156 | A | * | 5/1996 | Schulze ................. A61B 17/29 604/105 |

(Continued)

FOREIGN PATENT DOCUMENTS

| WO | WO 2003/013374 A1 |   | 2/2003 |   |
| WO | WO 2008/115288 | * | 9/2008 | ............. A61B 17/28 |

(Continued)

OTHER PUBLICATIONS

International Search Report and Written Opinion dated Apr. 14, 2015 in related PCT Application No. PCT/US2015/013216.

(Continued)

*Primary Examiner* — Sarah W Aleman
(74) *Attorney, Agent, or Firm* — Whiteford, Taylor & Preston, LLP; Gregory M. Stone

(57) ABSTRACT

Provided herein are expandable endoscopic devices. In accordance with certain aspects of an embodiment of the invention, an endoscopic expandable device is disclosed that comprises an expandable jaw at the distal tip, a control wire connected to the jaw, a sheath enclosing the control wire, and a handle connected to the sheath or wire having an actuating trigger. The expandable jaw is configured to allow its delivery in a retracted configuration to a target site within a patient's body through the working channel of an endoscope, after which the jaw may reconfigure to an expanded configuration that is larger than the retracted configuration. This allows the expandable jaw to be easily delivered to the target site while allowing an operable jaw size that is larger than would be allowed if limited to size of the working channel. The endoscopic expandable device may have utility as a clip or as forceps.

20 Claims, 12 Drawing Sheets

Related U.S. Application Data

(60) Provisional application No. 61/932,289, filed on Jan. 28, 2014.

(51) Int. Cl.
*A61B 17/22* (2006.01)
*A61B 10/04* (2006.01)
*A61B 17/128* (2006.01)
*A61B 17/122* (2006.01)
*A61B 17/10* (2006.01)
 *A61B 17/221* (2006.01)
 *A61B 17/00* (2006.01)

(52) U.S. Cl.
CPC ...... *A61B 17/1227* (2013.01); *A61B 17/1285* (2013.01); *A61B 17/22031* (2013.01); *A61B 2017/00269* (2013.01); *A61B 2017/00287* (2013.01); *A61B 2017/2215* (2013.01); *A61B 2017/2926* (2013.01); *A61B 2017/2931* (2013.01); *A61B 2017/2947* (2013.01)

(56) References Cited

U.S. PATENT DOCUMENTS

| | | |
|---|---|---|
| 5,549,639 A | 8/1996 | Ross |
| 5,891,152 A | 4/1999 | Sugarbaker et al. |
| 6,443,944 B1 * | 9/2002 | Doshi ............... A61B 17/29 600/143 |
| 8,287,554 B2 | 10/2012 | Cerier et al. |
| 2004/0116949 A1 | 6/2004 | Ewers et al. |
| 2005/0165429 A1 | 7/2005 | Douglas et al. |
| 2007/0197863 A1 | 8/2007 | Little |
| 2008/0269774 A1 | 10/2008 | Garcia et al. |
| 2009/0171380 A1 | 7/2009 | Whiting |
| 2010/0036380 A1 | 2/2010 | Taylor et al. |
| 2013/0046334 A1 | 2/2013 | Jones et al. |
| 2013/0282050 A1 | 10/2013 | Hart et al. |
| 2014/0330124 A1 | 11/2014 | Carol |

FOREIGN PATENT DOCUMENTS

| | | |
|---|---|---|
| WO | WO 2008/115288 A1 | 9/2008 |
| WO | WO 2009/136397 A2 | 11/2009 |
| WO | WO 2013/003256 A2 | 1/2013 |

OTHER PUBLICATIONS

Supplementary European Search Report for European Application No. 15 743 437.4, dated Oct. 9, 2017, 8 pgs.

Extended European Search Report, Application No. 17 198 794.4, dated Feb. 14, 2018, 8 pgs.

* cited by examiner

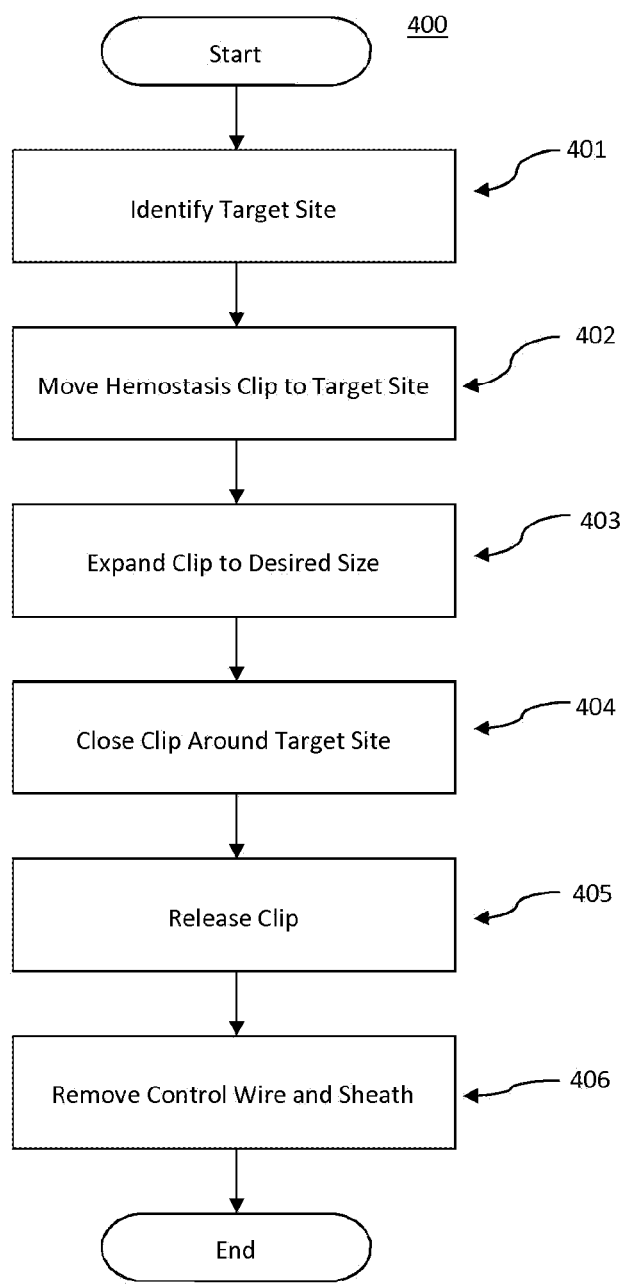

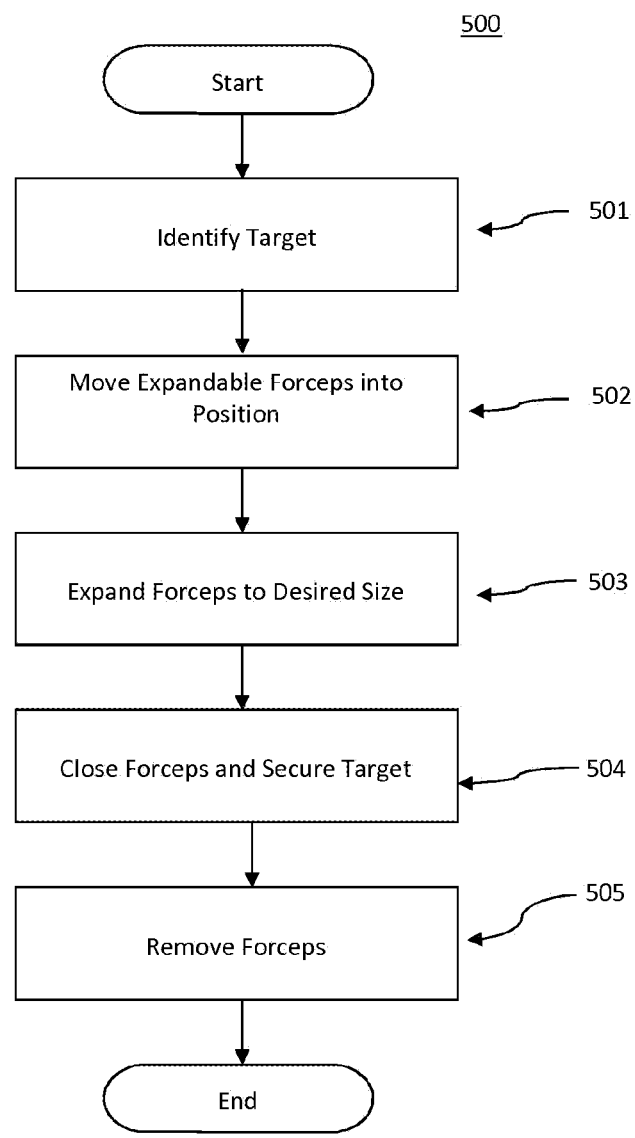

EXPANDABLE ENDOSCOPIC DEVICE

CROSS-REFERENCE TO RELATED APPLICATIONS

The present application is a continuation of U.S. Ser. No. 15/114,030, filed Jul. 25, 2016 which is a § 371 national stage application of PCT International Application No. PCT/US2015/013216, filed Jan. 28, 2015, which application claims a right of priority to U.S. Provisional Application No. 61/932,289, filed January 28, 201. All of the foregoing applications are hereby incorporated by reference.

FEDERALLY SPONSORED RESEARCH OR DEVELOPMENT

This work was supported by the U.S. Department of Veterans Affairs, and the Federal Government has certain rights in this invention.

FIELD OF THE INVENTION

The present invention relates generally to endoscopic devices. More specifically, the present invention relates to expandable endoscopic devices useful as clips and forceps.

BACKGROUND

Endoscopic forceps and clips are routinely used by endoscopists for mucosal biopsy and closure of a luminal defect created for therapeutic purposes or iatrogenically. The endoscopic approach is desirable in many circumstances because it is minimally invasive. However, the size of typical endoscopic clips and forceps are limited by the relatively small diameter of the working channel of commercially available endoscopes. Conventional biopsy forceps are limited to target areas of approximately five millimeters or less in diameter. The resection of larger tissue samples requires multiple passages. Conventional endoscopic clips are limited by the same constraints as conventional endoscopic forceps. As such, multiple clips may be needed to close larger defects. This may lead to complications and unnecessarily extends the time it takes to perform a procedure.

Accordingly, there is a need for endoscopic clips and forceps that fit within the working channel of a conventional endoscope, yet that are able to expand to a large enough size to fixate large defects, to remove large tissue samples, or to close mucosal defects in a single passage.

SUMMARY OF THE INVENTION

Provided herein are expandable endoscopic devices. In accordance with certain aspects of an embodiment of the invention, an endoscopic expandable device is disclosed that comprises an expandable jaw at the distal tip, a control wire connected to the jaw, a sheath enclosing the control wire, and a handle connected to the sheath or wire having an actuating trigger. The expandable jaw is configured to allow its delivery in a retracted configuration to a target site within a patient's body through the working channel of an endoscope (including, by way of non-limiting example, endoscopes used in urology, ENT applications, arthroscopy, laparascopic surgical procedures, and the like), after which the jaw may reconfigure to an expanded configuration that is larger than the retracted configuration. This allows the expandable jaw to be easily delivered to the target site while allowing an operable jaw size that is larger than would be allowed if limited to size of the working channel. The expandable jaw of the endoscopic expandable device may optionally be detachable from the sheath, in which case a jaw release mechanism may also be provided and controlled from the handle. The endoscopic expandable device described herein may, in accordance with certain aspects of the invention, have utility as a clip, and may, in accordance with further aspects of the invention, have utility as forceps. Also disclosed are methods of using the devices identified above.

In accordance with further aspects of an embodiment of the invention, an expandable endoscopic device is provided having a shaft extending in a first direction, an expandable grasping jaw assembly positioned at a distal end of the shaft, and a handle at a proximal end of the shaft, wherein the expandable grasping jaw assembly includes a plurality of grasping jaws expandable and retractable in a second direction perpendicular to the first direction.

In accordance with still further aspects of an embodiment of the invention, a method of using an expandable endoscopic device is provided, including the steps of providing an expandable endoscopic device having a shaft extending in a first direction, an expandable grasping jaw assembly positioned at a distal end of the shaft, and a handle at a proximal end of the shaft, wherein the expandable grasping jaw assembly includes a plurality of grasping jaws expandable and retractable in a second direction perpendicular to the first direction; moving the expandable endoscopic device to a target site within a patient; expanding the grasping jaw assembly around tissue at the target site; retracting the grasping jaw assembly of the expandable endoscopic device to a size smaller than the desired size; and removing at least a portion of the expandable endoscopic device from the patient.

BRIEF DESCRIPTION OF THE FIGURES

The above and other features, aspects, and advantages of the present invention are considered in more detail, in relation to the following description of embodiments thereof shown in the accompanying drawings, in which:

FIG. 4 is a flow chart representing an exemplary method for using the expandable endoscopic device of FIG. 1 as a clip.

FIG. 5 is a flow chart representing an exemplary method for using the expandable endoscopic device of FIG. 1 as forceps.

DETAILED DESCRIPTION

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form. Likewise, in the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Figure 1:
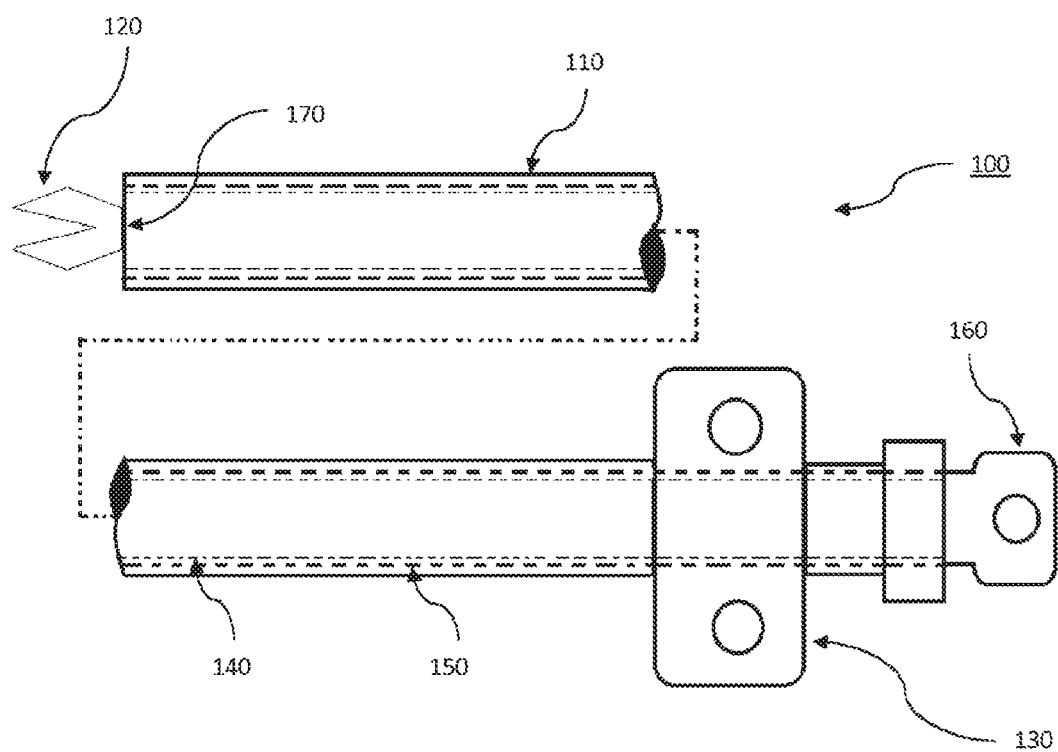
FIG. 1 is a schematic view of an expandable endoscopic device in accordance with certain aspects of an embodiment of the invention.

In accordance with certain aspects of an embodiment of the invention, FIG. 1 shows a schematic view of an endoscopic 100, which may be configured to remove a tissue sample or to close a perforation in a body. Expandable endoscopic device 100 includes an elongated shaft 110 made of generally flexible or pliable material, a working end 120 at the distal tip, and a handle 130 at the proximal end. Working end 120 may be configured for use as expandable forceps or as an expandable clip. Expandable endoscopic device 100 also preferably includes a control wire 140 extending through an axially rigid and preferably laterally bendable sheath 150, which in turn extends through elongated shaft 110. Control wire 140 is attached to the working end 120 at the distal tip and to handle 130 at the proximal end, and more preferably to an actuator in handle 130, as discussed in greater detail below. Control wire 140 may slide inside of sheath 150. Control wire 140 may be retracted into sheath 150 so that working end 120 may be fully or partially within sheath 150.

Particularly in those configurations in which working end 120 is configured as an expandable clip, the proximal end of medical device 100 may comprise a clip release actuator 160 configured to release working end 120 following placement. Clip release actuator 160 may be incorporated into handle 130 or it may be separate from handle 130. In those configurations of expandable endoscopic device 100 in which a clip release mechanism is provided, the clip release actuator 160 controls a clip release 170 located at the distal end of sheath 150. In the illustrated embodiment, the clip release 170 is centrally located. In other examples, there may be more than one clip release point located on the expandable clip located at the working end 120.

In some examples, the medical device 100 is sized to fit within the working channel of commercially available endoscopes. In other examples, the medical device 100 may be a stand-alone device. In stand-alone examples, the medical device 100 may further comprise one or more additional working channels.

Figure 2:
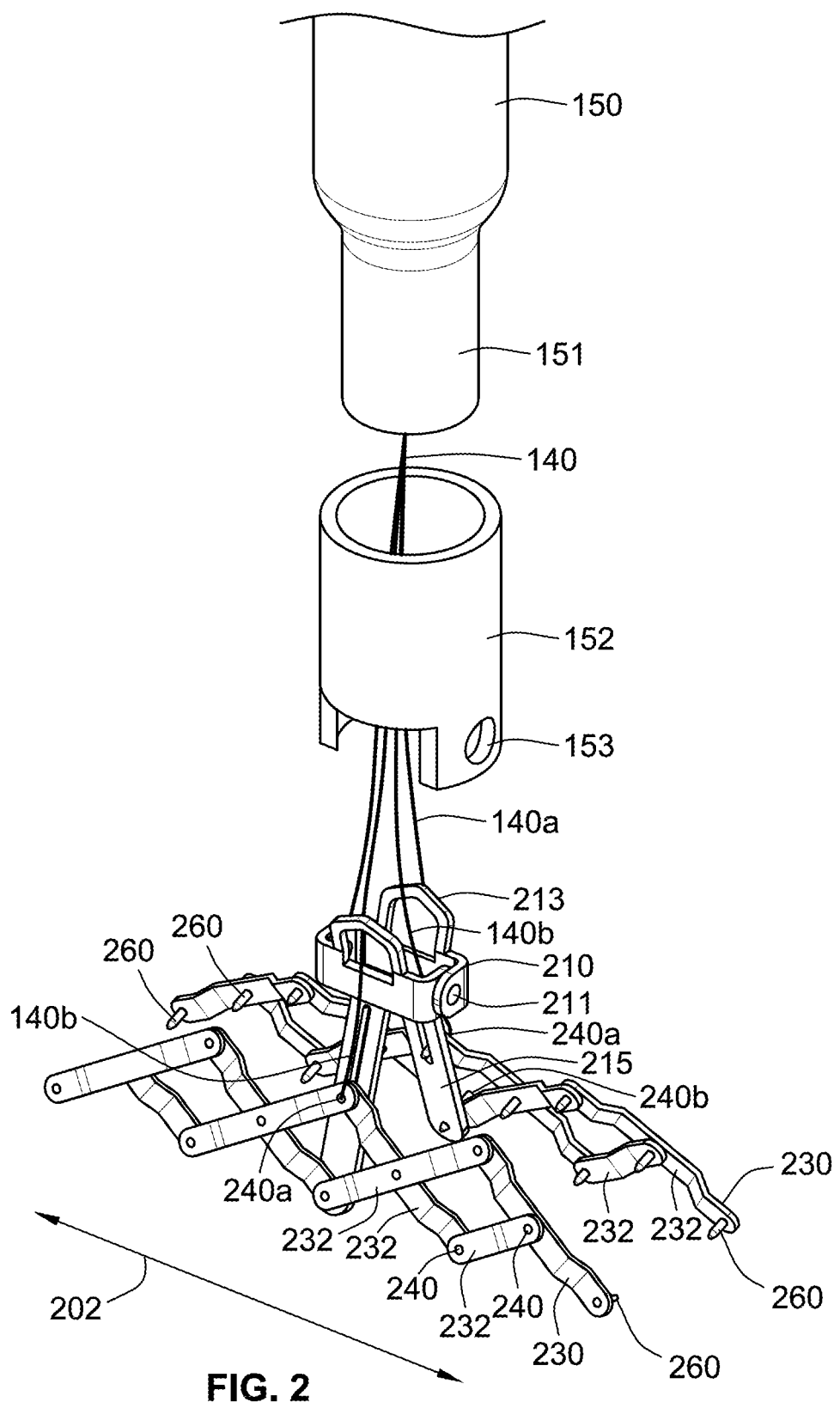
FIG. 2 is an exploded perspective view of the working end of the expandable endoscopic device of FIG. 1 in accordance with certain aspects of an embodiment of the invention.

FIG. 2 is an exploded perspective view of the working end of expandable endoscopic device 100 in accordance with certain aspects of an embodiment of the invention. An expandable jaw (shown generally at 200) is provided at the distal end of expandable endoscopic device 100, which expandable jaw 100 may expand and contract in a generally linear direction, outward from and perpendicular to a centerline of axially rigid, laterally bendable sheath 150, generally in the direction indicated by line 202. Expandable jaw 200 includes a base assembly 210 and two or more expansion arms 230. Base 210 of expandable jaw 200 may be connected to, and optionally detachably connected to, mount 152. Mount 152 is preferably fixed to a head 151 of sheath 150 having a slightly smaller outer diameter than that of sheath 150. The outer diameter of head 151 is likewise slightly less than the interior diameter of mount 152, such that mount 152 may be joined to head 151 of sheath 150 through use of (by way of non-limiting example) adhesive, welding, or such other connection methods as will be apparent to those skilled in the art.

Figure 7:
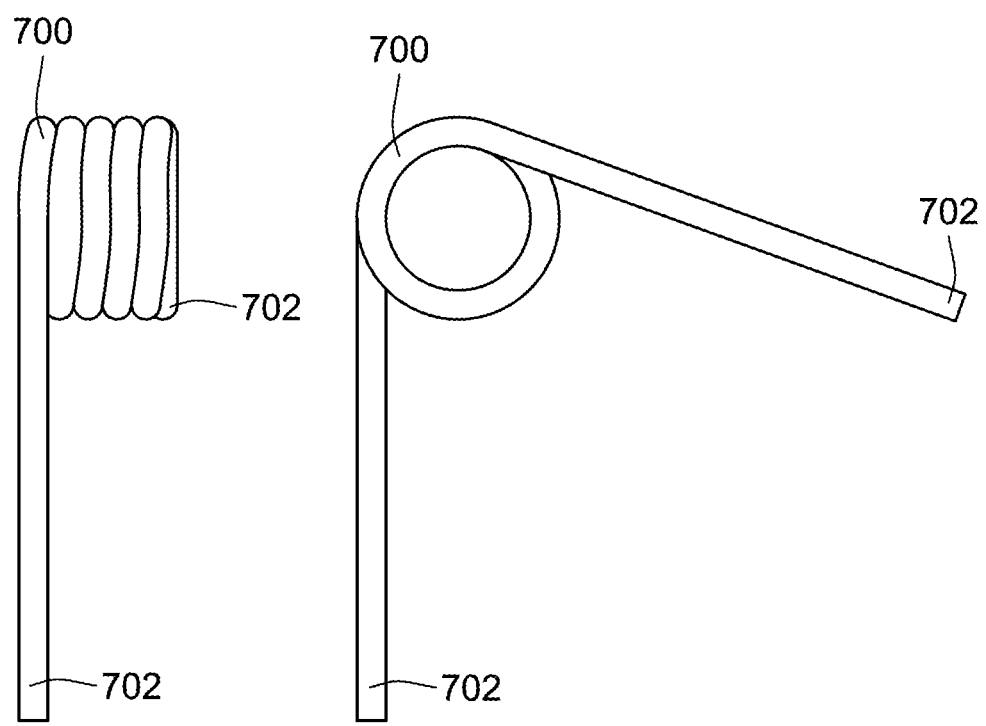
FIG. 7 is a close-up view of a torsion spring for use with the working end of FIG. 6.

A connecting pin 211 may extend across base 210, and likewise through openings 153 at a distal end of mount 152. Pin 211 also hingedly connects a first arm 212 of base 210 to second arm 213 of base 210, allowing arms 212 and 213 to pivot with respect to one another. First mounting arm 214 is attached to and extends distally from first arm 212, and is configured to mount one of expansion arms 230. Likewise, second mounting arm 215 is attached to and extends distally from second arm 213, and is configured to mount the other one of expansion arms 230. Thus, as first arm 212 and second arm 213 are pivoted toward one another, first mounting arm 214 and second mounting arm 215 will separate, in turn opening the jaw 200 formed by expansion arms 230. A torsion spring (FIG. 7) is preferably provided on an interior of base 210 and biases first arm 212 away from second arm 213, in turn biasing first mounting arm 214 and second mounting arm 215 (and thus the two expansion arms 230) toward one another and into a closed, clamping position. Alternatively, the spring may be positioned to bias first arm 212 toward second arm 213, in turn biasing the expansion arms away from one another and into an open, non-clamping position.

In order to operate expandable jaw 100 so as to open and close expansion arms 230, and to move expansion arms 230 between their expanded state (shown in FIG. 2) and their contracted state (and vice versa), control wires 140 extend through sheath 150 and outward from the distal end of sheath 150 to engage expandable jaw 100. A first set of control wires 140a attach to each of first arm 212 and second arm 213, and a second set of control wires 140b attach to each of expansion arms 230. In those configurations in which expandable jaw 200 is configured as an expandable clip, such that the clip is desired to be separable from sheath 150, control wires 140 are preferably detachable from first arm 212, second arm 213, and expansion arms 230, such as through activation of clip release actuator 160 discussed above. Likewise, in such detachable configuration, base 210 is preferably separable from mount 152, such as by having openings 153 at the bottom of mount 152 open to the distal end of mount 152 but with an opening width slightly less than the outer diameter of connecting pin 211. With this configuration, an operator may pull elongated shaft 110 away from expandable jaw 200 after it has been placed with sufficient force to cause connecting pin 211 to pass through the distal ends of openings 153, which (after separating of control wires 140 from expandable jaw 200) will allow sheath 150 and mount 152 to be removed while leaving expandable jaw 200 (in the form of a clip) in place. Other configurations allowing for the release of expandable jaw 200 from sheath 150 and mount 152, such as magnetic connections, frictional engagements, detent assemblies, and the like between either mount 152 and expandable jaw 200, or between sheath 150 and mount 152, may likewise be used without departing from the spirit and scope of the invention.

As mentioned above, control lines 140b attach to each of expansion arms 230 so as to cause expansion arms 230 to expand and contract, generally in the direction of arrow 202. FIG. 2 shows expandable jaw 100 in its expanded configuration. As control lines 140b are pulled towards the proximal end of the expandable endoscopic device (as further detailed below), expansion arms 230 contract in a scissors-type movement toward first mounting arm 214 and second mounting arm 215. In the fully collapsed or retracted configuration, the maximum length of each expansion arm 230 is sufficiently small so that sheath 150, mount 152, and the entire expandable jaw 200 may be initially passed through the endoscopic working channel from outside the patient and to the target site, and may likewise be retracted into the endoscopic working channel so as to allow for removal of expandable jaw 200 after its use.

In order to allow expansion arms 230 to so expand and contract, expansion arms 230 may be formed from a plurality of linkages 232 attached to one another at pivot joints 240. Pivot joints 240 allow individual linkages 232 to pivot with respect to one another in a direction that is perpendicular to the direction in which expansion arms 230 expand and contract. The particular number and size of linkages 232 and pivot joints 240 on a given expandable jaw 200 may vary, depending upon the desired size and use of the expandable jaw 200. A central, upper pivot joint 240a is provided as the center pivot joint for each expansion arm 230 closest to base 210, and is preferably configured to hold the second set of control wires 140b. Optionally and as discussed above, upper pivot joint 240a may be configured to detachably hold such second set of control wires 140b. A central, lower pivot joint 240b is likewise provided as the center pivot joint for each expansion arm 230 furthest from base 210. As second set of control wires 140b are pulled from the proximal end of expandable endoscopic device 100, upper pivot joint 240a is pulled upward and away from lower pivot joint 240b, in turn causing expansion arms 230 to retract toward each of first mounting arm 214 and second mounting arm 215. Upper pivot joint 240a may be biased toward lower pivot joint 240b, such as through use of a spring member attached to the two pivot joints, in turn biasing expandable jaw 200 toward the expanded state shown in FIG. 2. Alternatively, second set of control wires 140b may be sufficiently rigid so as to force upper pivot joint 240a toward lower pivot joint 240b when second set of control wires 140b is pushed toward the distal end of expandable endoscopic device 100.

Optionally, additional control wires may be provided and joined to additional pivot joints 240 as described above to further aid in expanding and contracting expansion arms 230. Likewise, additional control wires may be provided to engage the clip release 170 on expandable jaw 200 configured as discussed above.

Moreover, expandable arms 230 and joints 240 may optionally be configured to allow for retraction into the endoscopic working channel other than as configured above, such as by allowing the ends of expansion arms 230 to fold inward toward first mounting arm 214 and second mounting arm 215, such as by pivoting about central, upper pivot joint 240a so that expansion arms point in a direction parallel to sheath 150.

Expandable jaw 200 may also optionally include teeth 260 attached to an interior side of expansion arms 230. As shown in the configuration shown in FIG. 2, teeth 260 may extend perpendicularly from the interior face of expansion arms 230. Teeth 260 may likewise extend outward from the interior face of expansion arms 230 at various angles, such as (by way of non-limiting example) about 10°, 20°, 30°, 40°, 50°, 60°, 70°, 80°, 100°, 110°, 120°, 130°, 140°, 150°, 160°, or 170°. Teeth 260 may extend outward from the interior face of expansion arms 230 only in a plane that is perpendicular to a plane containing the interior face of each expansion arm 230, or may extend at a vertical angle and thus in a plane that is not perpendicular to the plane containing the interior face of each expansion arm 230. Teeth 260 may be located in sets of two, with each corresponding tooth 260 adjacent from one another so that when expandable jaw 200 is positioned at its intended site within a patient, each adjacently facing pair of teeth 260 comes together so that such pair of teeth 260 are touching. Optionally, teeth 260 may also include additional elements to provide for additional fixation, including by way of non-limiting example barbs or hooks. Further, the length and width of teeth 260 may vary and will depend upon the desired specifications for the clinician. The shape and orientation of teeth 260 may be uniform throughout the entire span of expansion arms 230, or some or all may differ in shape and/or orientation from one another. Likewise, teeth 260 may be eliminated altogether, in which case the interior faces of expansion arms 230 are used to secure or grasp the target area of the patient's anatomy. The interior faces of expansion arms 230 may be smooth or coarse.

Figure 3A:
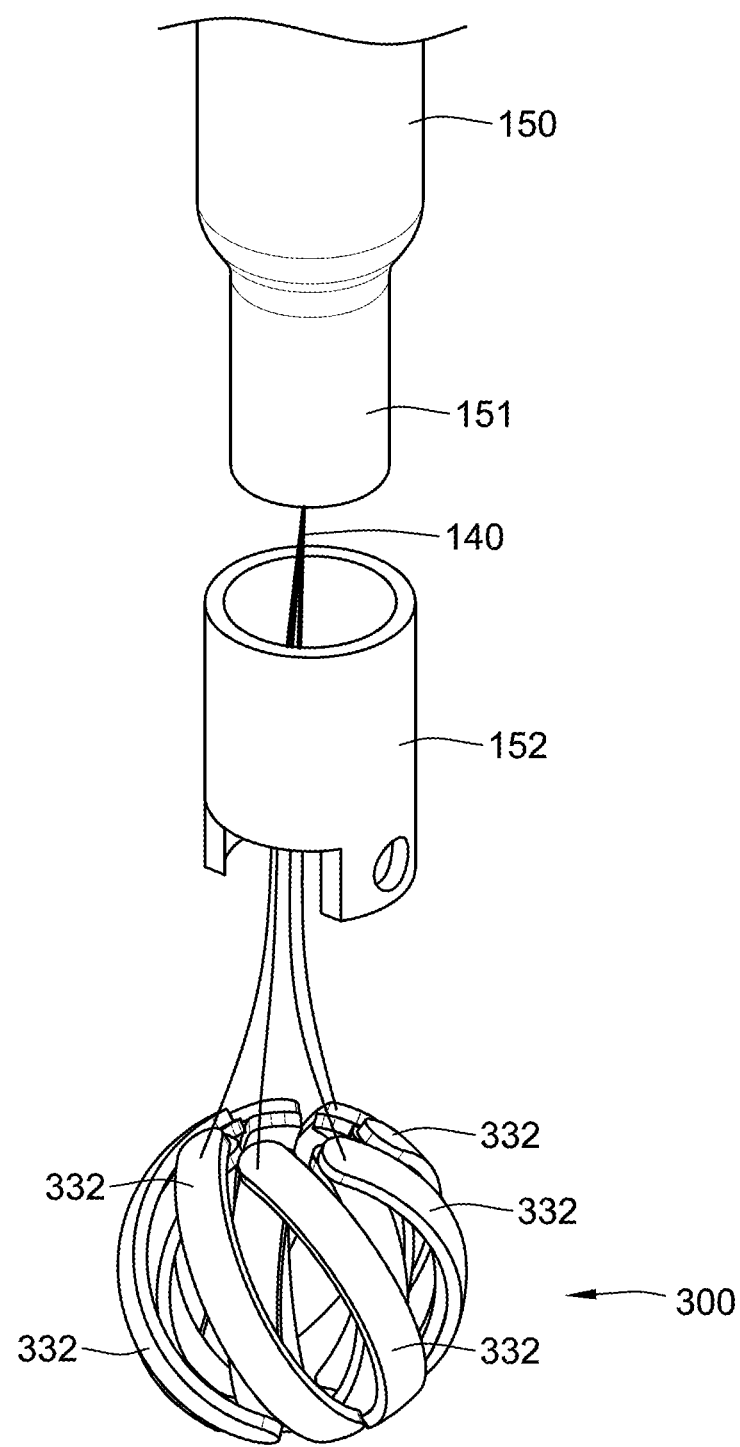
FIGS. 3a and 3b are an exploded perspective view and a top view, respectively, of the working end of the expandable endoscopic device of FIG. 1 in accordance with further aspects of an embodiment of the invention.
Figure 3B:
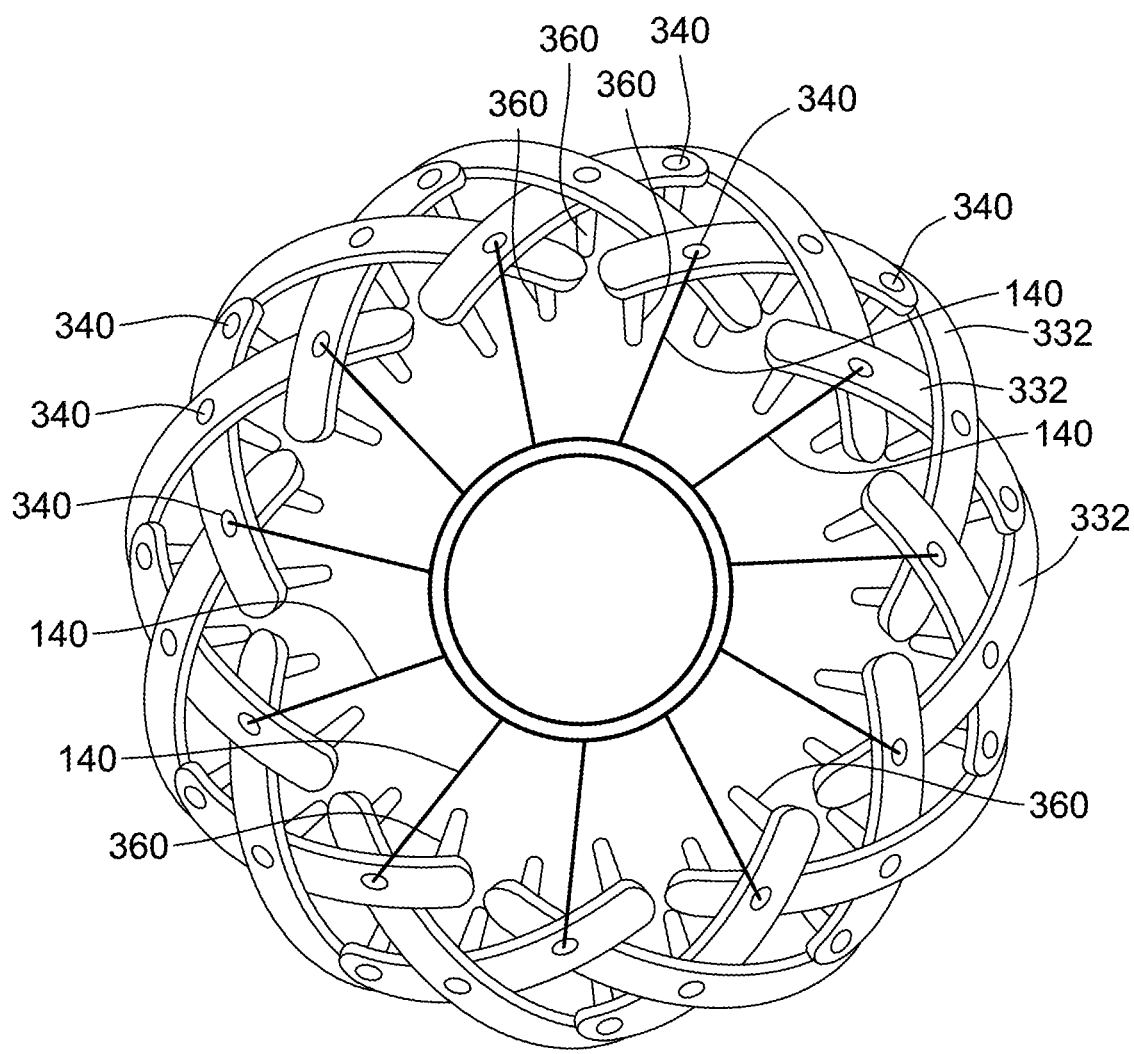

An alternative configuration for the expandable jaw of expandable endoscopic device 100 is shown in the perspective exploded view of FIG. 3a, in which expandable jaw 300 is provided as a round, and preferably circular, assembly that radially expands and contracts. While FIG. 3a shows expandable jaw 300 in its retracted configuration, FIG. 3b provides a top-down view of expandable jaw 300 in its expanded configuration. Expandable jaw 300 may be formed of three or more linkages 332 attached to one another by three or more joints 340. As shown in FIGS. 3a and 3b, linkages 332 are curved and are pivotably connected to one another by joints 340 so as to form a generally circular shape. Alternatively, linkages 332 may be connected to one another so as to form an elliptical or polygonal shape. The curvature of individual linkages 332, and the number and location of joints 340, may vary so as to optimize the expanded configuration of expandable jaw 300 for various applications.

As with linearly expandable jaw 200, radially expandable jaw 300 may likewise be provided a plurality of teeth 360 attached to an interior face of linkages 332, which again may vary in size and orientation as described above with respect to teeth 260. Likewise, teeth 360 may be eliminated altogether, in which case the interior faces of linkages 332 are used to secure or grasp the target area of the patient's anatomy. The interior faces of linkages 332 may be smooth or coarse.

In order to operate radially expandable jaw 300, control wires 140 are again provided that extend from the distal end of mount 152 (which in turn is positioned at the distal end of sheath 150), which control wires 140 are attached to one or more of the upper most (i.e., closest to mount 152) joints 340, such that pulling guide wires 140 toward the proximal end of expandable endoscopic device 100 will result in radially expandable jaw 300 retracting toward the retracted configuration shown in FIG. 3, allowing expandable jaw 300 to be retracted to engage tissue inside of a patient's body, and further retracted into the fully retracted position of FIG. 3a so that it may pass through the endoscopic working channel. Radially expandable jaw 300 may optionally be spring biased toward the fully expanded configuration of FIG. 3b, or one or more of control wires 140 may be sufficiently rigid so that pushing the control wires 140 from the proximal end of expandable endoscopic device 100 and toward the distal end will cause expandable jaw 300 to move toward the expanded configuration of FIG. 3b.

Optionally, radially expandable jaw 300 may also be separable from sheath 150 using a release configured as described above with regard to linearly expandable jaw 200.

Further, when linearly expandable jaw 200 or radially expandable jaw 300 is configured for use as forceps, one or more spikes (not shown) may be provided extending distally from base 210 (in the linearly expandable jaw 200 configuration) or from the distal end of sheath 150 (in the radially expandable jaw 300 configuration). Such spikes are generally provided a sharp point at the distal end, but may have a different shape so long as the spike shape assists with securing the target site. The length and diameter of the spike may vary, but the spike is preferably no larger than what can be housed inside of the arms of the forceps without impeding the other moving parts.

FIG. 4 provides a flow chart depicting a first exemplary method for using an expandable endoscopic device 100 as described above, and particularly when such expandable endoscopic device 100 is configured for use as a clip. In this configuration, the expandable clip may be used to stop acute bleeding and hemostasis in a patient's gastrointestinal tract. However, this example should be understood as only one of the many implications for which an expandable endoscopic clip as described herein might be used. It would be understood by those of ordinary skill in the art that not all of the steps recited in the flow chart of FIG. 4 would be necessary in order to perform the operation. One would also recognize that the identified steps may be conducted in a different order without impacting the effectiveness of the procedure.

In step 401, the clinician identifies a target in need of hemostatic clipping. Next, in step 402, an expandable endoscopic clip configured as above is moved to the target site. With regard to certain aspects of an exemplary embodiment, the expandable endoscopic clip is entered through a working channel of an endoscope. In step 403, the clip is expanded to the necessary size. With regard to further aspects of an exemplary embodiment, the size of the clip is expanded, such as (by way of non-limiting example) by pushing control wires 140 toward the distal end of sheath 150. In step 404, the expandable endoscopic clip is closed to bring the jaws of the device together. With regard to still further aspects of an exemplary embodiment, the clip is closed by pulling the control wires 140 toward the proximal end of the expandable endoscopic device 100. Optionally, once the clip has secured the trauma site, in step 405 the expandable endoscopic clip is released by the clip release mechanism, and at step 406 the remaining assembly is removed from the endoscope.

Likewise, FIG. 5 provides a flow chart depicting a first exemplary method for using an expandable endoscopic device 100 as described above, and particularly when such expandable endoscopic device 100 is configured for use as forceps. Once again, it would be understood by those of ordinary skill in the art that not all of the steps recited in the flow chart of FIG. 5 would be necessary to perform the operation. One would also recognize that the identified steps may be conducted in a different order without impacting the effectiveness of the procedure.

In step 501, the clinician identifies a trauma site requiring application of the expandable forceps. Next, in step 502, the expandable forceps are moved to the target site. With regard to certain aspects of an exemplary embodiment, the expandable forceps are entered through a working channel of an endoscope. In step 503, the expandable forceps are expanded to the necessary size. With regard to further aspects of an exemplary embodiment, the size of the forceps are expanded, such as (by way of non-limiting example) by pushing control wires 140 toward the distal end of sheath 150. In step 504, the expandable forceps are closed to bring the jaws of the device together, such as by pulling the control wires 140 toward the proximal end of the expandable endoscopic device 100. In step 505, the expandable forceps, sheath 150, and the remaining assembly is removed from the patient by the clinician.

Figure 6:
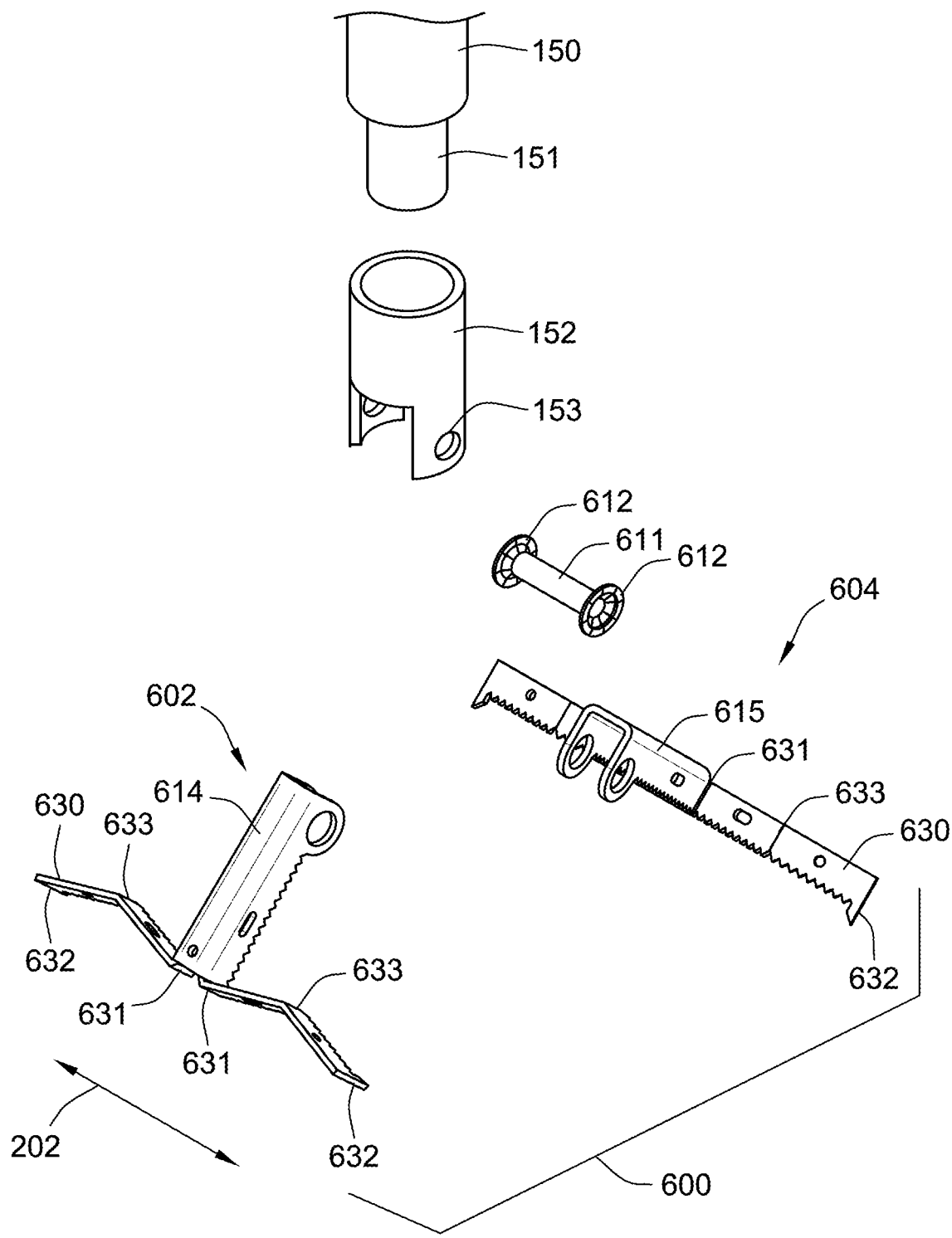
FIG. 6 is an exploded perspective view of the working end of the expandable endoscopic device of FIG. 1 in accordance with further aspects of an embodiment of the invention.

FIG. 6 is an exploded perspective view of the working end of expandable endoscopic device 100 in accordance with still further aspects of an embodiment of the invention. An expandable jaw (shown generally at 600) is provided at the distal end of expandable endoscopic device 100, which expandable jaw 600 may expand and contract in a generally linear direction, outward from and perpendicular to a centerline of axially rigid, laterally bendable sheath 150, generally in the direction indicated by line 202. Expandable jaw 600 includes first expansion arm 602 and second expansion arm 604, each of which are connected to, and optionally detachably connected to, mount 152, which in turn is preferably fixed to head 151 of sheath 150 as described above.

A connecting pin 611 may extend through openings 153 at a distal end of mount 152. Connecting pin 611 may have flanged outer walls 612 that, when assembled in mount 152, rest against an exterior wall of mount 152 to hold connecting pin 611 in place. Pin 611 also hingedly connects a first arm 614 of first expansion arm 602 to second arm 615 of second expansion arm 604, and both expansion arms 602 and 604 to mount 152, allowing first expansion arm 602 and second expansion arm 604 to pivot with respect to one another. A torsional spring 700 (shown in FIG. 7) is preferably mounted around connecting pin 611 so that the arms 702 of torsional spring 700 rest against the interior faces of first arm 614 and second arm 615, in turn biasing first arm 614 preferably away from second arm 615, and thus biasing first expansion arm 602 away from second expansion arm 603 into an open-jaw position.

Mounted at a distal end of each of first arm 614 and second arm 615 are linearly expanding grasper jaws 630, each of which extend outward from the distal end of each of first arm 614 and second arm 615. Each grasper jaw 630 is preferably formed of superelastic nitinol, a memory metal capable of deforming and readily returning to its intended shape after removal of the deforming force. Each segment of grasper jaws 630 is joined at a first edge 631 to the base of its respective arm 614 or 615, and extends outward from such arm 614 or 615. Approximately midway between first edge 631 and an outer edge 632 is a bend 633, such that in the natural (i.e., non-stressed) configuration, each grasper jaw 630 extends initially upward as it extends away from arm 614 or 615 until it reaches bend 633, at which point it turns downward as it extends out to outer edge 632. Bend 633 provides a collapsing point for each segment of grasper jaws 630, such that as the outer edges 632 are pulled toward arms 614 or 615 (as discussed in greater detail below), each segment of grasper jaws 630 will fold along such bend 633, allowing grasper jaws 630 to retract toward arms 614 and 615 so as to achieve a maximum length that will allow it to pass through the endoscopic working channel so that expandable jaw 600 may be both moved to the target site from outside the patient, and ultimately removed from the patient after the particular operation is completed.

Figure 8:
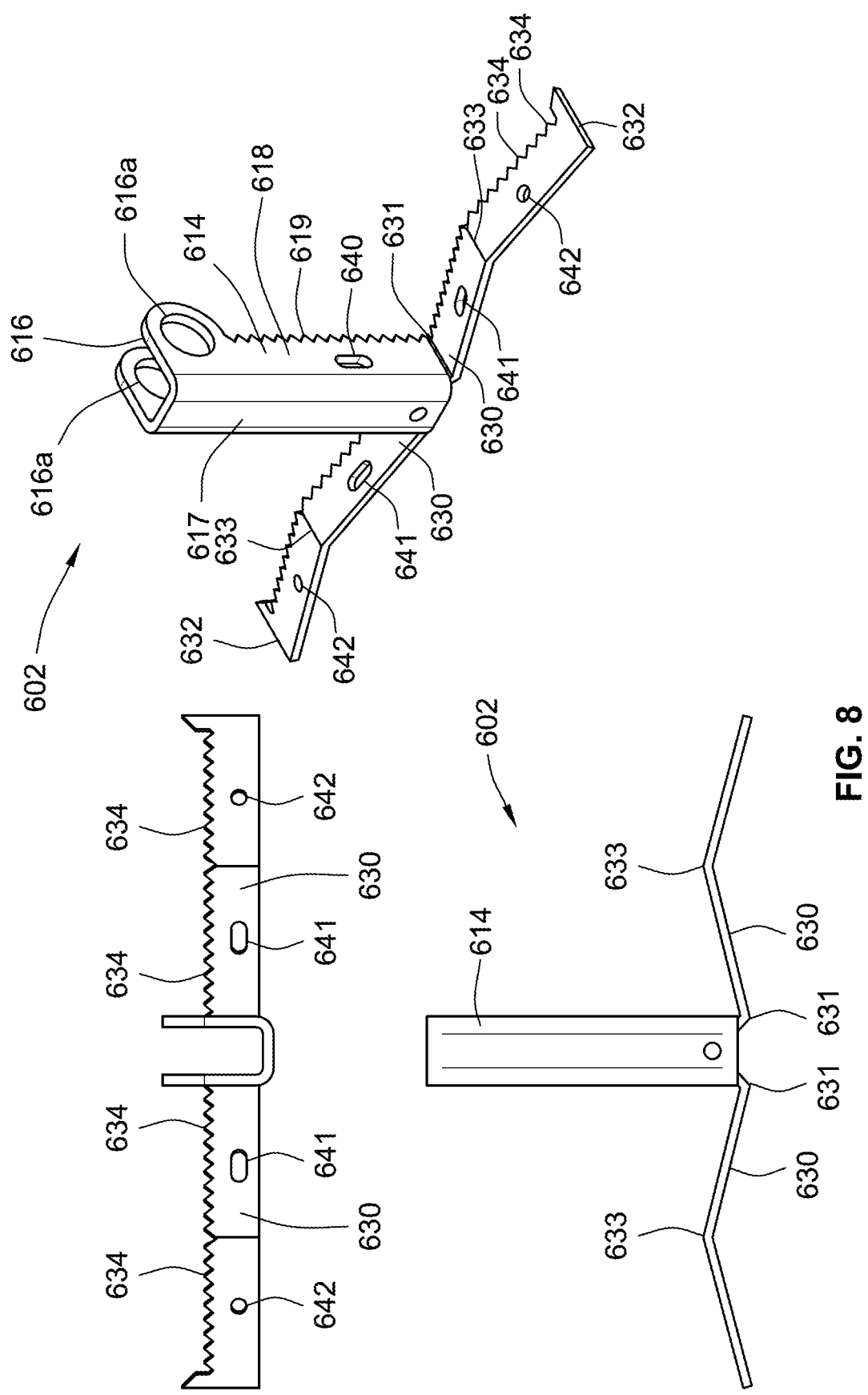
FIG. 8 is a close-up view of a first grasping jaw for use with the working end of FIG. 6.
Figure 9:
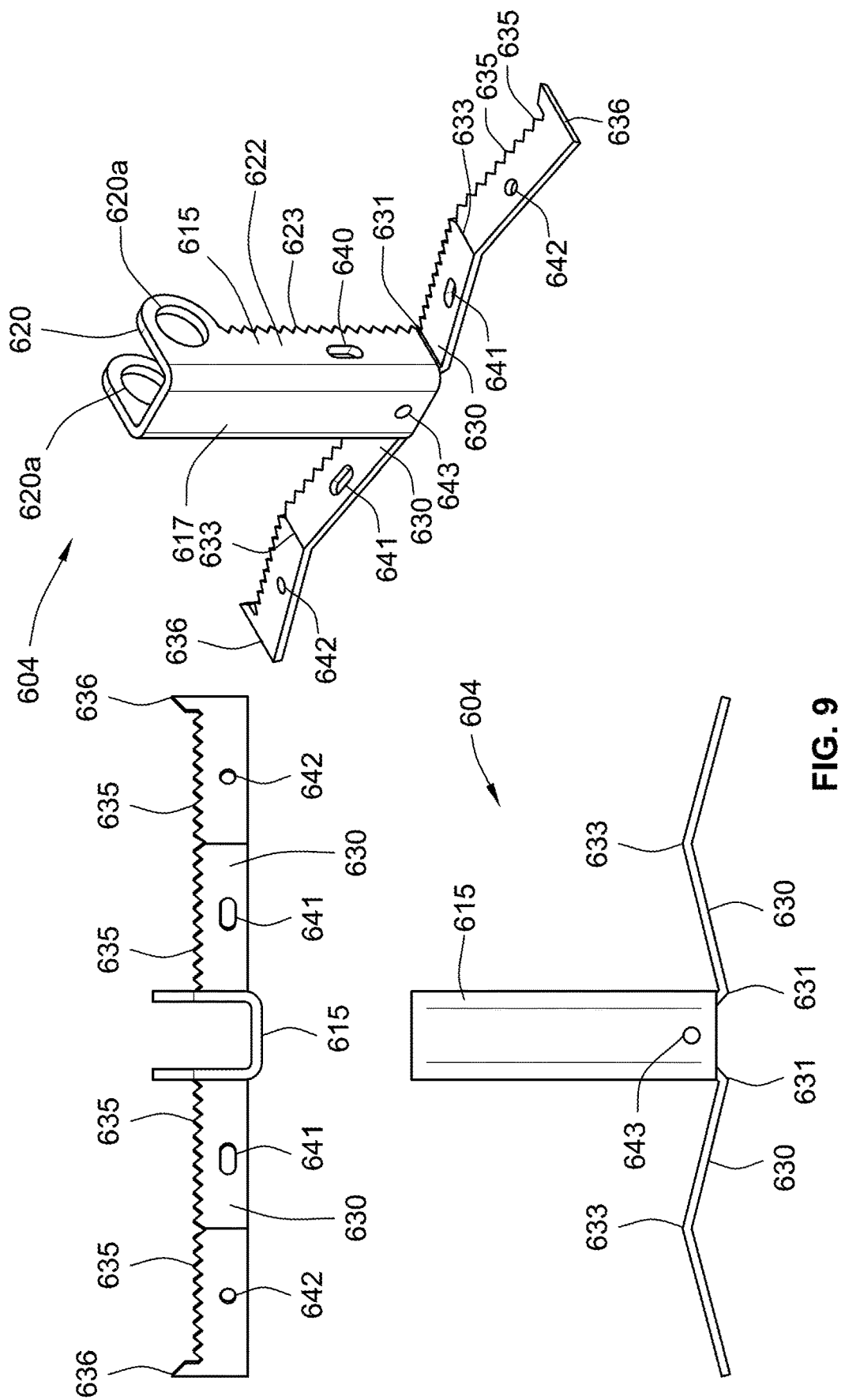
FIG. 9 is a close-up view of a second grasping jaw for use with the working end of FIG. 6.

FIG. 8 provides various close-up views of first expansion arm 602, and FIG. 9 provides various close-up views of second expansion arm 604.

With particular reference to FIG. 8, first expansion arm 602 includes first arm 614 having a head portion 616 with openings 616a extending across the head portion 616 to receive connecting pin 611. First arm 614 has a planar back wall 617 and side walls 618. An interior edge 619 of side walls 618 is provided a series of gripping teeth configured to mate with complementary teeth on the interior edges 623 of side walls 622 of second expansion arm 604 when the two expansion arms 602 and 604 are brought together into a closed, clamping configuration. Grasper jaws 630 are joined to the bottom edge of first arm 614 at the base of each side wall 618, and as shown in the front view of first expansion arm 602 of FIG. 8, may initially extend upward from the base of each side wall 618 at an angle of, for example, 75°, and may turn downward at bend 633 at an angle of, for example, 30°. An interior edge of each grasper jaw 630 is provided a series of gripping teeth 634 configured to mate with complementary teeth 635 on the interior edges of grasper jaws 630 on second expansion arm 604 (FIG. 9).

A plurality of openings 640, 641, and 642 are provided for receiving control wires 140 therethrough for manipulating first expansion arm 602. More particularly, an opening 640 is provided in each side wall 618 through which a first control wire 140b may pass to engage the adjacent grasper jaw 630. Likewise, another opening 641 is positioned through the first segment of each grasper jaw 630 that is adjacent each side wall 618, through which the control wire 140b that has been passed through opening 640 may be threaded. Finally, an opening 642 is provided in the outer segment of each grasper jaw 630, which may receive the end of the control wire 140b that has been passed through openings 640 and 641. Such control wire 140b is fixed to opening 642, such that pulling on that control wire 140b toward the proximal end of expandable endoscopic device 100 will result in retraction of grasper jaws 630 towards first arm 614, as discussed further below. Additionally, an opening 643 is provided in back wall 617 of first arm 614, to which is joined a separate control wire 140a which may be pulled toward the proximal end of expandable endoscopic device 100 to cause pivoting of first expansion arm 602 toward second expansion arm 604 and into a closed, clamping configuration.

Likewise, with particular reference to FIG. 9, second expansion arm 604 includes second arm 615 having a head portion 620 with openings 620a extending across the head portion 620 to receive connecting pin 611. Openings 620a align with opening 616a of first expansion arm 602 when the two expansion arms are assembled onto mount 152. Likewise, head portion 620 is slightly larger than head portion 616 of first expansion arm 602, such that head portion 616 of first expansion arm 602 may fit inside of head portion 620 of second expansion arm 604. Second arm 615 has a planar back wall 621 and side walls 622. An interior edge 623 of side walls 622 is provided a series of gripping teeth configured to mate with complementary teeth on the interior edges 619 of side walls 618 of first expansion arm when the two expansion arms 602 and 604 are brought together into a closed, clamping configuration. Grasper jaws 630 are joined to the bottom edge of second arm 615 at the base of each side wall 622, and as shown in the front view of second expansion arm 604 of FIG. 9, may initially extend upward from the base of each side wall 622 at an angle of, for example, 75°, and may turn downward at bend 633 at an angle of, for example, 30°. While such angles may vary, it is preferable for the profiles of grasper jaws 630 on each of first expansion arm 602 and second expansion arm 604 to match so as to be able to form a tight, closed, clamping configuration. An interior edge of each grasper jaw 630 on second expansion arm 604 is likewise provided a series of gripping teeth 635 configured to mate with the complementary teeth 634 on the interior edges of grasper jaws 630 on second expansion arm 604 (FIG. 9). Additionally, an oversized tooth 636 or other projection is preferably provided on an outermost edge of each grasper jaw 630 of second extension arm 604, which is configured to help guide grasper jaws 630 of first extension arm 602 into proper engagement with grasper jaws 630 of second expansion arm 604.

As with first expansion arm 602, a plurality of openings 640, 641, and 642 are provided for receiving control wires 140 therethrough for manipulating second expansion arm 604. More particularly, an opening 640 is provided in each side wall 622 through which a first control wire 140b may pass to engage the adjacent grasper jaw 630. Likewise, another opening 641 is positioned through the first segment of each grasper jaw 630 that is adjacent each side wall 622, through which the control wire 140b that has been passed through opening 640 may be threaded. Finally, an opening 642 is provided in the outer segment of each grasper jaw 630, which may receive the end of the control wire 140b that has been passed through openings 640 and 641. Such control wire 140b is fixed to opening 642, such that pulling on that control wire 140b toward the proximal end of expandable endoscopic device 100 will result in retraction of grasper jaws 630 towards second arm 615, as discussed further below. Additionally, an opening 643 is provided in back wall 621 of second arm 615, to which is joined a separate control wire 140a which may be pulled toward the proximal end of expandable endoscopic device 100 to cause pivoting of second expansion arm 604 toward first expansion arm 602 and into a closed, clamping configuration.

Figure 10:
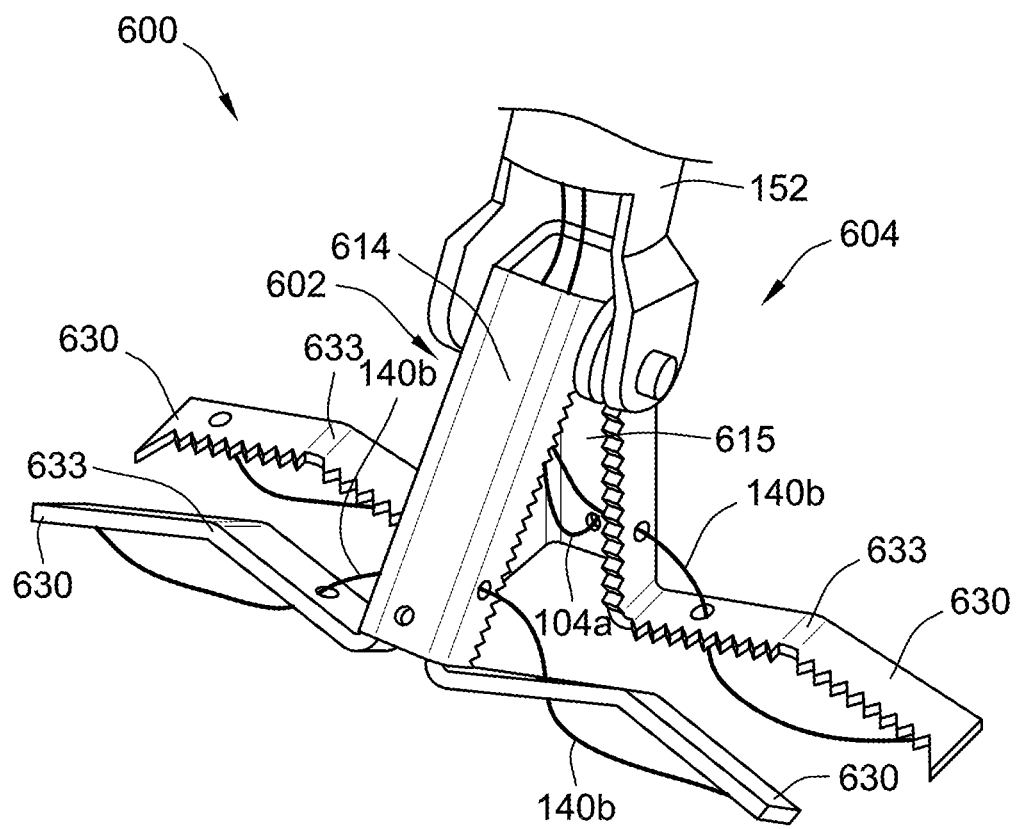
FIG. 10 is a close-up perspective view of the working end of FIG. 6 in an assembled condition.

FIG. 10 provides a close-up perspective view of expandable jaw 600, including control wires 140 positioned to manipulate first expansion arm 602 and second expansion arm 604 as described above. Each control wire 140 may be joined to its respective opening 642, 643 by way of adhesive bonding, such as by way of non-limiting example through use of cyanoacrylate adhesive, although other forms of bonding control wires 140 to first and second expansion arm 602 and 604 will be readily apparent to those of ordinary skill in the art. In order to operate expandable jaw 600 so as to open and close expansion arms 602 and 604, and to move grasper jaws 630 between their expanded state (shown in FIG. 10) and their contracted state, control wires 140 extend through sheath 150 and outward from the distal end of sheath 150 and mount 152 to engage expandable jaw 600. A first set of control wires 140a attach to each of first arm 614 and second arm 615, and a second set of control wires 140b attach to each of grasper jaws 630 as described above.

As control lines 140b are pulled towards the proximal end of the expandable endoscopic device (as further detailed below), grasper jaws 630 fold inward at bend 633 toward first arm 614 and second arm 615. In the fully collapsed or retracted configuration, the maximum length of each grasper jaw 630 is sufficiently small so that sheath 150, mount 152, and the entire expandable jaw 600 may be retracted into the endoscopic working channel so as to allow for removal of expandable jaw 600 after its use.

As grasper jaws 630 are preferably formed of a memory metal such as nitinol, grasper jaws 630 may be initially folded into their collapsed or retracted position when initially placed within the endoscopic working channel and/or elongated shaft 110, and they will automatically expand to the open configuration shown in FIG. 10 when they exit the endoscopic working channel and/or elongated shaft 110 (i.e., when the constraining force on the outer edges of grasper jaws 630 is removed), thus easily allowing delivery of expandable jaw 600 to its intended sight through the endoscopic working channel.

Moreover, and again as a result of grasper jaws 630 being formed of a memory metal such as nitinol, expandable jaw 600 may still be removed through an endoscopic working channel even if control wires 140b are not provided or are damaged or inadvertently detached during use. More particularly, as sheath 150 and mounts 152 are retracted and pulled into the endoscopic working channel, the interior walls of the channel will press against grasper jaws 630, pushing them forward (bending them about edge 631) and thus still allowing full retraction of the expandable jaw 600 into and through the endoscopic working channel after its use.

Figure 11:
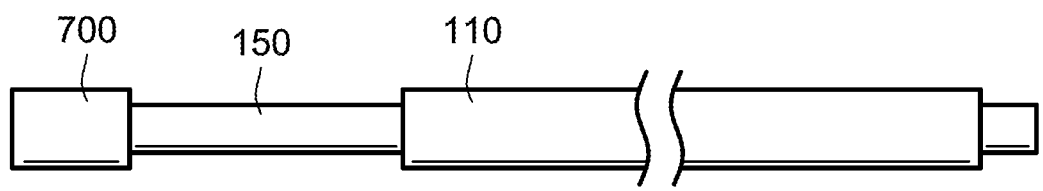
FIG. 11 is a side view of a cable assembly for use with the expandable endoscopic device of FIG. 1.

FIG. 11 is a side view of an exemplary cable system for interconnecting the working end of expandable endoscopic device 100 to handle 130. As shown in FIG. 11, such cable system preferably includes a handle attachment section 700 which may be used to affix the cable assembly to handle 130 (as discussed in further detail below), axially rigid, laterally bendable sheath 150, and elongated shaft 110. Elongated shaft 110 may comprise an FDA-compliant, heat-shrink, acrylated olefin material surrounding sheath 150. Likewise, sheath 150 is preferably in the form of a tightly wound, stainless steel spring that has sufficient stiffness to provide a guide channel in which guide wires 140 may move without binding, sufficient compressive axial rigidity so that it may push the working end of expandable endoscopic device through the endoscopic working channel and into engagement with the intended tissue within a patient's body, and at least some laterally bending flexibility to allow for positioning and movement through the endoscopic working channel.

Figure 12:
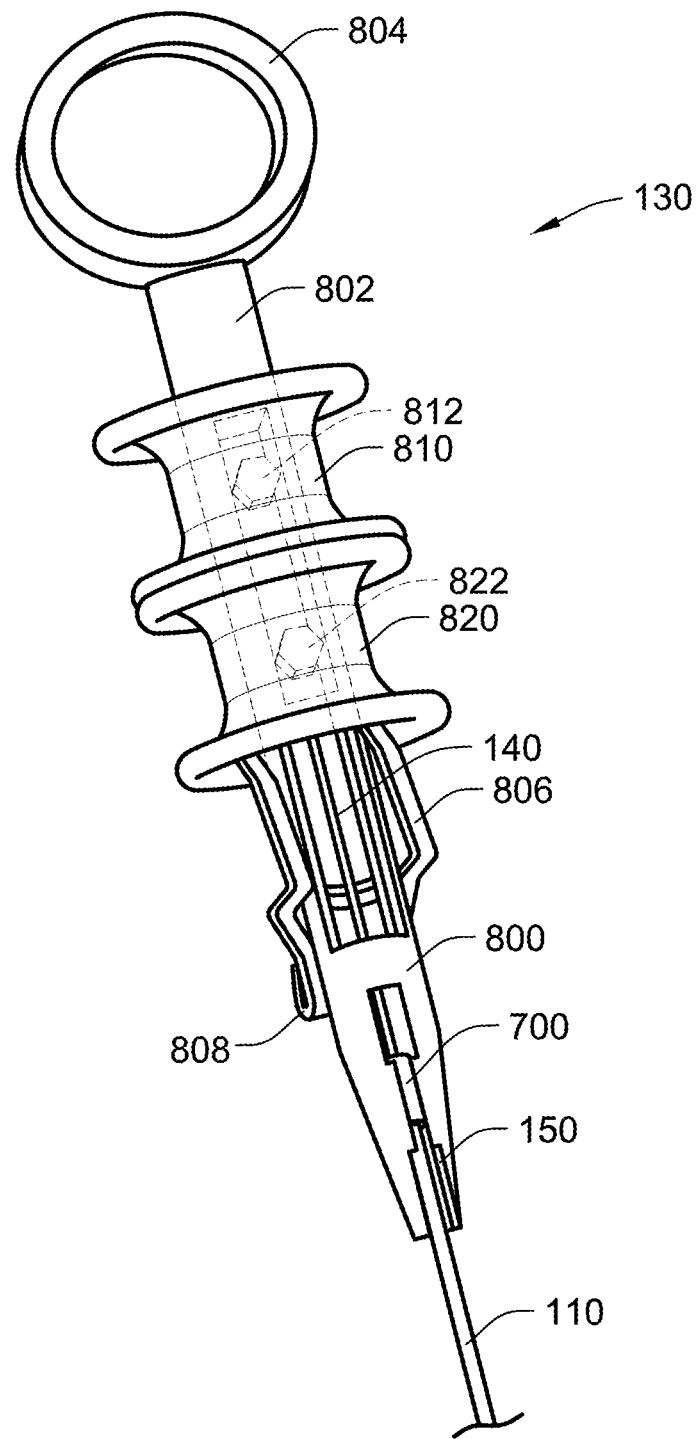
FIG. 12 is a perspective view of a handle for use with the expandable endoscopic device of FIG. 1.

FIG. 12 is a perspective view of an exemplary handle 130 for use with the expandable endoscopic device 100. Handle 130 includes a cable receiver 800 that receives handle attachment section 700 of the interconnecting cable system of FIG. 11 and fixedly attaches handle attachment section 700 to cable receive 800, such as by crimping, adhesive, welding, or such other attachment mechanisms as will occur to those of ordinary skill in the art. Control wires 140 extend from the upper end of handle attachment section 700 and are fixedly attached to one of actuator rings 810 or 820, each of which are laterally movable along a shaft 802 of handle 130. For example, control wires 140a, which engage the jaw clamping function at the working end 120 of expandable endoscopic device 120, may be joined to first actuator ring 810, such as by clamping the control wires 140a on an interior of first actuator ring 810 with a set screw 812. Likewise, control wires 140b, which engage the folding/retracting function at the working end 120 of expandable endoscopic device 120, may be joined to second actuator ring 820, such as by clamping the control wires 140b on an interior of second actuator ring 820 with a set screw 822. In this configuration, first actuator ring 810 may be grasped, with an operator placing their thumb through thumb ring 804 and engaging first actuator ring 810 with, for example, their index and middle fingers, pulling first actuator ring 810 toward thumb ring 804 to close the clamping jaws at the working end 120 and in turn grab the intended tissue at the target site within the patient and hold that tissue during whatever operation is being performed. After the operation is completed, the operator may then engage second actuator ring 820 in similar manner, drawing it upward toward first actuator ring 810 and thumb ring 804, which in turn will cause the expandable jaws at the working end 120 to retract inward to a maximum length that will allow their passage through the endoscopic working channel. A hinged spring lock 806 may be provided which is hingedly connected to shaft 802 at a lower end of shaft 802, which spring lock 806 may be flipped upward to engage the bottom face of second actuator ring 820 when it is in its fully retracted position. This will maintain the working end 120 in its retracted position, allowing easy removal of the entire assembly once the medical procedure has been completed.

Optionally, a single actuator ring 810 may be provided when working end 120 is configured having grasper jaws 630 formed of a memory metal, such as nitinol, as the working end may fold to allow its withdrawal through the endoscopic working channel simply as a result of its contact with the working channel as described above.

The example embodiments of the expandable endoscopic device described herein may be used for a number of different implications. When configured for use as an expandable clip, the expandable endoscopic device described herein may be used to treat acute bleeding and hemostasis. The expandable clip may also be used to close mucosal defects following endoscopic procedures such as, for example, an endoscopic sumucosal dissection, or an endoscopic mucosal resection. The expandable clip may also be used to close openings of full thickness wall closure following procedures such as, for example, laparoscopic procedures, percutaneous endoscopic jejunostomy, and percutaneous endoscopic gastrostomy, in various systems including the gastrointestinal, genitourinary, and respiratory systems.

Likewise, when configured for use as expandable forceps, the expandable endoscopic device described herein may be used to obtain tissue biopsies from the gastrointestinal, genitourinary, and respiratory tracts. The expandable forceps may also be used to perform a polypectomy, an endoscopic mucosal resection, or an endoscopic submucosal dissection.

One having ordinary skill in the art would recognize other potential uses for the various embodiments of the device described herein. It should be understood that these uses do not deviate from the broader spirit and scope of this invention. The specific dimensions of the device will depend on the implication for which it is being used. The shape and size of the expandable endoscopic device and its component parts will depend, in part, on the size and orientation of the target site. These parameters will control the size and design of the working parts. The device may be designed for a single use or it may be reusable.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. An expandable endoscopic device, comprising:
   a shaft extending from a proximal end to a distal end, the distal end of the shaft extending in a first direction;
   an expandable grasping jaw assembly positioned at the distal end of the shaft, the expandable grasping jaw assembly having a first grasping jaw pivotably mounted relative to a second grasping jaw for rotation about an axis extending in a second direction non-parallel to the first direction, the first and second grasping jaws operable between open and closed positions to grasp objects therebetween; and
   a handle at the proximal end of said shaft operably connected to the grasping jaw assembly;
   wherein each of the first and second grasping jaws are expandable and retractable in the second direction between expanded and retracted configurations to adjust the size of the expandable grasping jaw assembly in the second direction;
   wherein the first grasping jaw comprises a first arm and first and second grasper jaw segments, the first arm being pivotably mounted to the distal end of the shaft for rotation about the axis, the first grasper jaw segment extending outward from a first side of the first arm and pivotally connected thereto about a first pivot axis that is non-parallel to the axis, the second grasper jaw segment extending outward from the first grasper jaw segment and pivotally connected thereto about a second pivot axis that is non-parallel to the axis;
   wherein the second grasping jaw comprises a second arm and third and fourth grasper jaw segments, the second arm being pivotably mounted to the distal end of the shaft for rotation about the axis, the third grasper jaw segment extending outward from a first side of the second arm and pivotally connected to the second arm about a third pivot axis that is non-parallel to the axis, the fourth grasper jaw segment extending outward from the third grasper jaw segment and pivotally connected thereto about a fourth pivot axis that is non-parallel to the axis;
   wherein, upon operation from the expanded configuration to the retracted configuration, outer edges of the first and third grasper jaw segments rotate proximally and inwardly towards the first and second arms, and outer edges of the second and fourth grasper jaw segments rotate distally and inwardly towards the first and second arms.

2. The expandable endoscopic device of claim 1, wherein the first, second, third and fourth grasper jaw segments are formed as flat plates, and wherein the first and second grasper jaw segments lie flat against the first arm in the retracted configuration, and wherein the third and fourth grasper jaw segments lie flat against the second arm in the retracted configuration.

3. The expandable endoscopic device of claim 1, further comprising a first control wire operatively connected to the handle, wherein the first arm includes an aperture and the first grasper jaw segment includes an aperture between its ends, and wherein the first control wire extends through the shaft, through the aperture of the first arm, through the aperture of the first grasper jaw segment, and is connected to the second grasper jaw segment such that tension on the control wire operates the first grasping jaw from its expanded configuration to its retracted configuration.

4. The expandable endoscopic device of claim 3, wherein the first and second grasper jaw segments are biased outwardly away from the first arm and towards the expanded configuration.

5. The expandable endoscopic device of claim 3, further comprising a second control wire operatively connected to the handle, wherein the second arm includes an aperture and the third grasper jaw segment includes an aperture between its ends, and wherein the second control wire extends through the shaft, through the aperture of the second arm, through the aperture of the third grasper jaw segment, and is connected to the fourth grasper jaw segment such that tension on the second control wire operates the second grasping jaw from its expanded configuration to its retracted configuration.

6. The expandable endoscopic device of claim 5, wherein the third and fourth grasper jaw segments are biased outwardly away from the second arm and towards the expanded configuration.

7. The expandable endoscopic device of claim 6, wherein the first and second grasping jaws are formed of nitinol.

8. The expandable endoscopic device of claim 1, wherein the first grasper jaw segment and the second grasper jaw segment are foldable inward toward the first arm accordion-style.

9. The expandable endoscopic device of claim 1, wherein the first grasper jaw segment and the second grasper jaw segment each have an interior face facing the second jaw, and each the interior face further comprises serrated teeth along each the interior face.

10. The expandable endoscopic device of claim 9, wherein the teeth are configured to mate with complementary teeth on the second grasping jaw.

11. The expandable endoscopic device of claim 1, wherein the first grasping jaw further comprises fifth and sixth grasper jaw segments, the fifth grasper jaw segment extending outward from a second side of the first arm opposite the first side, the fifth grasper jaw segment pivotally connected to the first arm about a fifth pivot axis that is non-parallel to the axis, the sixth grasper jaw segment extending outward from the fifth grasper jaw segment and pivotally connected thereto about a sixth pivot axis that is non-parallel to the axis; and
   wherein the second grasping jaw comprises seventh and eighth grasper jaw segments, the seventh grasper jaw segment extending outward from a second side of the second arm opposite the first side, the seventh grasper jaw segment pivotally connected to the second arm about a seventh pivot axis that is non-parallel to the axis, the eighth grasper jaw segment extending outward from the seventh grasper jaw segment and pivotally connected thereto about an eighth pivot axis that is non-parallel to the axis.

12. The expandable endoscopic device of claim 1, wherein the first and second grasping jaws, in the retracted configuration, have a retracted length that is less than the deployed jaw length.

13. The expandable endoscopic device of claim of claim 12, wherein the retracted length is sufficiently small to allow passage of the jaw assembly through a working channel of an endoscope through which the shaft extends.

14. The expandable endoscopic device of claim 1, wherein the first and second grasping jaws are pivotally mounted about a pin defining the axis.

15. The expandable endoscopic device of claim 1, wherein the grasping jaw assembly is detachable from the shaft.

16. The expandable endoscopic device of claim 1, wherein, in the expanded configuration, the first and second grasper jaw segments are coplanar and project orthogonally from the first arm, and the third and fourth grasper jaw segments are coplanar and project orthogonally from the second arm.

17. An expandable endoscopic device, comprising:
- a shaft extending from a proximal end to a distal end, the distal end of the shaft extending in a first direction;
- an expandable grasping jaw assembly positioned at the distal end of the shaft, the expandable grasping jaw assembly having a first grasping jaw pivotally mounted relative to a second grasping jaw for rotation about an axis extending in a second direction non-parallel to the first direction, the first and second grasping jaws operable between open and closed positions to grasp objects therebetween;
- a handle at the proximal end of said shaft operably connected to the grasping jaw assembly;
- a first control wire having a first end operatively connected to the handle and a second end operatively connected to the expandable grasping jaw assembly; and
- a second control wire having a first end operatively connected to the handle and a second end operatively connected to the expandable grasping jaw assembly;
- wherein each of the first and second grasping jaws are expandable and retractable in the second direction between expanded and retracted configurations to adjust the size of the expandable grasping jaw assembly in the second direction;
- wherein the first grasping jaw comprises a first arm and first and second grasper jaw segments, the first arm being pivotably mounted to the distal end of the shaft for rotation about the axis, the first and second grasper jaw segments pivotally connected to each other and the first arm, the first control wire attached to the second grasper jaw segment such that tension on the first control wire causes the first and second grasper jaws segments to collapse inwardly against the first arm in the retracted configuration;
- wherein the second grasping jaw comprises a second arm and third and fourth grasper jaw segments, the second arm being pivotably mounted to the distal end of the shaft for rotation about the axis, the third and fourth grasper jaw segments pivotally connected to each other and the second arm, the second control wire attached to the fourth grasper jaw segment such that tension on the second control wire causes the third and fourth grasper jaws segments to collapse inwardly against the second arm in the retracted configuration.

18. The expandable endoscopic device of claim 17, wherein the first, second, third and fourth grasper jaw segments are formed as flat plates, and wherein the first and second grasper jaw segments lie flat against the first arm in the retracted configuration, and wherein the third and fourth grasper jaw segments lie flat against the second arm in the retracted configuration.

19. The expandable endoscopic device of claim 17, wherein the first and second grasper jaw segments are biased outwardly away from the first arm and towards the expanded configuration, and wherein the third and fourth grasper jaw segments are biased outwardly away from the second arm and towards the expanded configuration.

20. The expandable endoscopic device of claim 17, wherein the first grasper jaw segment and the second grasper jaw segment are foldable inward toward the first arm accordion-style.

* * * * *